(12) United States Patent
Mink et al.

(10) Patent No.: US 9,833,425 B2
(45) Date of Patent: Dec. 5, 2017

(54) GENTISIC ACID IS USED TO IMPROVE SYSTEMIC HEMODYNAMICS, HEPATIC MITOCHONDRIAL FUNCTION AND LACTATE ACIDEMIA IN PATIENTS WITH SEPTIC SHOCK

(71) Applicant: UNIVERSITY OF MANITOBA, Winnipeg (CA)

(72) Inventors: Steven Mink, Winnipeg (CA); Paul Fernyhough, Winnipeg (CA)

(73) Assignee: University of Manitoba, Winnipeg, MB (CA)

( * ) Notice: Subject to any disclaimer, the term of this patent is extended or adjusted under 35 U.S.C. 154(b) by 0 days.

(21) Appl. No.: 15/277,483

(22) Filed: Sep. 27, 2016

(65) Prior Publication Data

US 2017/0128398 A1  May 11, 2017

Related U.S. Application Data

(60) Provisional application No. 62/233,749, filed on Sep. 28, 2015.

(51) Int. Cl.
*A61K 31/192* (2006.01)
*A61P 31/00* (2006.01)
*A61K 9/00* (2006.01)

(52) U.S. Cl.
CPC .......... *A61K 31/192* (2013.01); *A61K 9/0019* (2013.01)

(58) Field of Classification Search
CPC ............................ A61K 31/192; A61K 9/0019
USPC ..................................... 514/236.2
See application file for complete search history.

(56) References Cited

U.S. PATENT DOCUMENTS

2012/0277312 A1* 11/2012 Mink ................... A61K 31/235
514/544

\* cited by examiner

*Primary Examiner* — Kristin Vajda
(74) *Attorney, Agent, or Firm* — Ade & Company Inc.; Michael R. Williams

(57) ABSTRACT

Gentisic acid sodium salt is shown to be useful as a treatment to improve systemic hemodynamics, hepatic mitochondrial function and lactic acidemia in patients with septic shock.

5 Claims, 8 Drawing Sheets

GENTISIC ACID IS USED TO IMPROVE SYSTEMIC HEMODYNAMICS, HEPATIC MITOCHONDRIAL FUNCTION AND LACTATE ACIDEMIA IN PATIENTS WITH SEPTIC SHOCK

PRIOR APPLICATION INFORMATION

The instant application claims the benefit of U.S. Provisional Patent Application Ser. No. 62/233,749, filed Sep. 28, 2015 and entitled "GENTISIC ACID IS USED TO IMPROVE SYSTEMIC HEMODYNAMICS, HEPATIC MITOCHONDRIAL FUNCTION AND LACTATE ACIDEMIA IN PATIENTS WITH SEPTIC SHOCK", the contents of which are incorporated herein by reference.

BACKGROUND OF THE INVENTION

The development of lactic acidemia (LA) in septic shock (SS) is associated with an ominous prognosis (1). Blood concentrations of lactate depend on the rates of its production and utilization by various organs (2). In an experimental canine model of SS, we previously showed that production of lactate by the splanchnic organs increased in this model, while hepatic uptake of lactate was impaired (3). The mechanism by which hepatic impairment may occur in SS is not clear. Uptake of lactate by the liver occurs by means of a membrane-associated, pH-dependent, bidirectional facilitative antiport transport system known as the monocarboxylate transporter (MCT) (4-6). MCT1 is highly expressed in the liver. In the condition in which there is increased production of lactate by means of the glycolytic pathway in the liver, lactate could exit the hepatocyte by means of MCT, while there would be a cotransport of hydroxyl (OH) anions into the cell. This would lead to excess hydrogen ions into the extracellular space and the clinical syndrome of LA (see FIG. 1A). On the other hand, hepatic uptake of lactate by MCT would produce a cotransport of OH ions into the extracellular space ions and a correction of LA. The extent to which MCT protein may be altered in SS has never been studied.

Once transported into the hepatocyte by MCT, lactate can be shuttled into the Cori-cycle for gluconeogenesis or can be converted to pyruvate to enter the mitochondria to be metabolized to $CO_2$ and water (6) (see FIG. 1). Mitochondrial dysfunction has been postulated as an explanation for the development of LA in SS, although this has been not universally accepted (7-15). In mitochondria, electrons are transferred primarily by reduced nicotinamide adenine dinucleotide (NADH) to mitochondrial complexes I, III, and IV to generate a proton ($H^+$) gradient (the proton motive force; pmf) across the mitochondrial inner membrane. The free energy accumulated as the pmf is then used to drive ATP synthesis through the F1FoATP synthase activity (Complex V) allowing protons to return to the mitochondrial matrix (12-13).

The variable results previously reported in the literature about the presence of mitochondrial dysfunction in SS may be a consequence of the different methodology and experimental protocols that were used in these studies. The recent development of the Seahorse XF24 extracellular flux analyzer that we used in the present study allows for precise measurements of mitochondrial oxygen consumption under various conditions and has not previously been used to investigate mitochondrial dysfunction in SS (17).

SUMMARY OF THE INVENTION

According to an aspect of the invention, there is provided a method of treating an individual who has or is believed to have or at risk of developing septic shock comprising administering to said individual an effective amount of gentisic acid or a pharmaceutically acceptable salt thereof.

According to another aspect of the invention, there is provided use of gentisic acid or a pharmaceutically acceptable salt thereof for treating sepsis or septic shock.

According to another aspect of the invention, there is provided use of gentisic acid or a pharmaceutically acceptable salt thereof for the preparation of a medicament for treating sepsis or septic shock.

According to another aspect of the invention, there is provided a method of preparing a medicament for treating sepsis or septic shock comprising admixing gentisic acid or a salt thereof, for example, an effective amount of gentisic acid or a salt thereof, with a pharmaceutically acceptable carrier, diluent or excipient.

According to an aspect of the invention, there is provided a method of treating an individual who has or is believed to have or at risk of developing lactic acidernia comprising administering to said individual an effective amount of gentisic acid or a pharmaceutically acceptable salt thereof. The individual may be an individual with sepsis or septic shock.

According to another aspect of the invention, there is provided use of gentisic acid or a pharmaceutically acceptable salt thereof for treating lactic acidemia.

According to another aspect of the invention, there is provided use of gentisic acid or a salt thereof for the preparation of a medicament for treating lactic academia.

According to another aspect of the invention, there is provided a method of preparing a medicament for treating lactic acidemia comprising admixing gentisic acid or a salt thereof, for example, an effective amount of gentisic acid or a salt thereof, with a pharmaceutically acceptable carrier, diluent or excipient.

DESCRIPTION OF THE PREFERRED EMBODIMENTS

Figure 1:
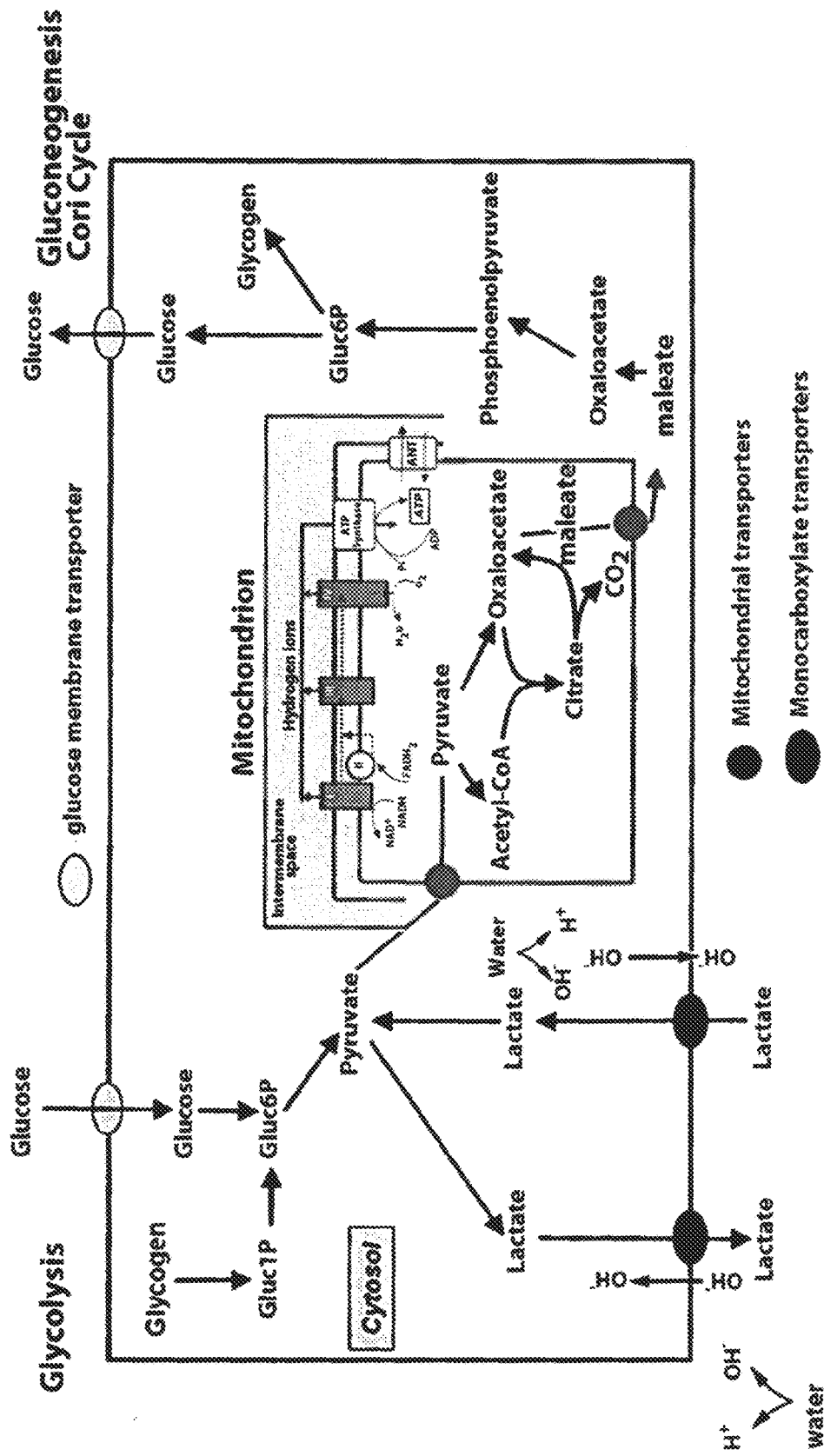
FIG. 1. In this schematic of a hepatocyte, lactate is taken up into the cell by the mononcarboxylate transporter. Uptake of lactate is accompanied by an efflux of the hydroxyl ion ($OH^-$) and vice versa. Once inside the cell, lactate can be converted to pyruvate and can enter the mitochondrion for metabolism by the citric acid cycle to carbon dioxide and water (6). During oxidative phosphorylation, hydrogen ions are transported into the intermembrane space by complexes (I, III, IV) of the electron transport chain and ATP are generated by ATP synthase. ATP is transferred out of the mitochondria by adenine nucleotide translocase (ANT), since ATP within the mitochondria can inhibit oxygen consumption rate (OCR). Lactate can also be generated from glycolysis (11,12), where Gluc1P and Glu6P are glucose 1 phosphate and glucose 6 phosphate respectively. Lactate contained within the cytosol can also be converted into glucose by the Cori cycle.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Based on the numerous questions raised in the literature about the pathogenesis of LA in SS, we used a canine model in the present study to address the following questions. We first determined whether the development of LA in this model of SS was associated with hepatic mitochondrial dysfunction. Secondly, we determined whether LA could be directly related to the accompanying systemic hypotension that occurs in which we administered the vasopressor norepinephrine (NE) to reverse hypotension (18). Thirdly, we measured hepatic MCT1 protein concentrations to determine whether changes in MCT1 contributed to the presence of LA in sepsis. Finally, we previously showed that select phenolic compounds have unique physiological properties in our sepsis models, likely attributable to their antioxidant capabilities in which they are able to reverse the systemic vasodilation and hence low mean blood pressure (MAP) that occurs (19-20). We found that gentisic acid sodium salt (GSS) (see FIG. 2A), could not only reverse the low MAP that occurs in our sepsis model, but could also decrease blood lactate concentrations. We then compared the efficacy of GSS on systemic hemodynamics, LA, and hepatic mitochondrial function in our canine model with those of NE to determine whether GSS could be used as a treatment of cardiovascular collapse and LA in SS.

In anesthetized/ventilated dogs, we infused the bacteria over ~1.0 hrs in various treatment groups (see below). We isolated the hepatic mitochondria and measured mitochondrial oxygen consumption rates using the novel Seahorse XF24 analyzer under conditions that included: basal respiration, after the addition of adenosine-diphosphate to produce coupled respiration, and after the addition of a protonophore to produce maximal respiration. We found that in the septic control group, mitochondrial dysfunction developed in which there was a reduction in maximal respiration. While both NE and GSS increased MAP and maximal respiration in respective groups, only GSS caused an increase in coupled respiration and a reduction in LA. There was no change in MCT protein among the groups.

Mitochondrial depression occurs in SS, but does not appear to be the sole mechanism for the development of LA, since NE improved mitochondrial depression without reversing LA. GSS, a phenolic compound restored MAP, mitochondrial depression, and LA in SS. As discussed herein, GSS is useful in the treatment of septic shock.

As demonstrated herein, gentisic acid or a pharmaceutically acceptable salt thereof can be used as a treatment to improve systemic hemodynamics, improve hepatic mitochondrial function, restore blood pressure and improve lactate acidemia in patients with septic shock.

According to an aspect of the invention, there is provided a method of treating an individual who has or is believed to have or at risk of developing septic shock comprising administering to said individual an effective amount of gentisic acid or a pharmaceutically acceptable salt thereof.

As will be appreciated by one of skill in the art, as used herein, an "effective amount" of gentisic acid is an amount of gentisic acid or a pharmaceutically acceptable salt thereof that is sufficient to reduce the severity of at least one symptom associated with septic shock, for example but by no means limited to reduced serum lactate, increased blood pressure, improved systemic hemodynamics, improved hepatic mitochondria function, reduced severity or incidence of lactic acidemia and the like.

As will be appreciated by one of skill in the art, the "effective amount" will depend on the age, weight, general condition and severity of illness of the individual. However, it is of note that the effective amount can be determined through routine experimentation.

A person at believed to have or at risk of having septic shock is an individual who has sepsis. Individuals at the greatest risk of developing sepsis are children, the elderly and immunocompromised individuals.

According to another aspect of the invention, there is provided use of gentisic acid or a pharmaceutically acceptable salt thereof for treating sepsis or septic shock.

According to another aspect of the invention, there is provided use of gentisic acid or a salt thereof for the preparation of a medicament for treating sepsis or septic shock.

According to another aspect of the invention, there is provided a method of preparing a medicament for treating sepsis or septic shock comprising admixing gentisic acid or a salt thereof, for example, an effective amount of gentisic acid or a salt thereof, with a pharmaceutically acceptable carrier, diluent or excipient.

According to an aspect of the invention, there is provided a method of treating an individual who has or is believed to have or at risk of developing lactic acidemia comprising administering to said individual an effective amount of gentisic acid or a pharmaceutically acceptable salt thereof. The individual may be an individual with sepsis or septic shock.

For example, treating lactic acidemia may involve reduction in lactate levels to below 5 mmol/L and elevation of serum pH to above 7.35.

According to another aspect of the invention, there is provided use of gentisic acid or a pharmaceutically acceptable salt thereof for treating lactic acidemia.

According to another aspect of the invention, there is provided use of gentisic acid or a salt thereof for the preparation of a medicament for treating lactic acidemia.

According to another aspect of the invention, there is provided a method of preparing a medicament for treating lactic acidemia comprising admixing gentisic acid or a salt thereof, for example, an effective amount of gentisic acid or a salt thereof, with a pharmaceutically acceptable carrier, diluent or excipient.

In a preferred embodiment, an effective amount of the medicament, that is, the an effective amount of the pharmaceutical composition comprising genitisic acid or a pharmaceutically acceptable salt thereof and a pharmaceutically acceptable carrier, diluent or excipient, is administered to an individual in need of such treatment, such as for example the individual who is suffering from or is at risk of developing lactic acidemia or sepsis or septic shock, as discussed herein.

As discussed herein, GSS is a novel molecule that can increase blood pressure, reverse mitochondrial dysfunction, and attenuate lactate academia in SS. This is the first molecule of its kind that has similar type of properties and is useful in the treatment of SS.

We designed this study to address several questions. One objective was to determine whether hepatic mitochondrial dysfunction developed in this model of SS. In this study, we showed that after approximately 10 hrs of bacteremia in this model, there was evidence that mitochondrial dysfunction had evolved. Specifically, there was a significant reduction in maximal respiration observed in the septic control group, while basal respiration and mitochondrial complex IV enzymatic activity also appeared depressed. Coupled respiration did not decline. In the literature, the question of whether mitochondrial dysfunction develops in SS has been debated. In an earlier study, Yuda and colleagues (25) did not observe a reduction in either hepatic or skeletal muscle mitochondrial respiration when they measured the respiration of several mitochondrial complexes in a fecal model of porcine peritonitis. On the other hand, in an endotoxemic rabbit model and in bacteremic baboons, Gellerich and colleagues (26) described abnormalities of mitochondrial function when they performed enzymatic measurements on similar mitochondrial complexes in skeletal muscle. Although the explanation for differences in the literature is not clear and may be a consequence of the diverse models and methodologies used, most of the previous studies have concentrated on coupled respiration as their primary index of mitochondrial function. In contrast, our results demonstrate that uncoupled respiration may be a more sensitive parameter to reflect mitochondrial dysfunction in sepsis. In SS, because of the high metabolic energy demands that occur, mitochondrial ATP may be utilized as quickly as it is formed. Since there would be no feedback of ATP on inhibiting ATP synthase activity, uncoupled maximal respiration may be a more representative measurement of what happens in the clinical situation.

Besides the finding of a reduction in maximal OCR in this sepsis model, another objective was to determine whether NE treatment could reverse this effect. We found that in the NE septic group, the addition of NE to maintain MAP near baseline resulted in an augmentation of maximal OCR to an extent comparable to that observed in the non-septic control group. NE treatment could prevent mitochondrial dysfunction by increasing hepatic oxygen delivery, thereby preventing oxidant damage produced by ischemic hypoxia, or by an intrinsic effect. In the literature, the effect of NE on mitochondrial function in sepsis has been controversial. Regueira and colleagues (27) found that in an endotoxemic pig model, the administration of NE was associated with an improvement of hepatic mitochondrial respiration. They concluded that this effect was probably mediated by a direct effect of NE on liver cells. NE has been shown to cause an increase in calcium transport into the mitochondrial matrix (28). Calcium can stimulate three different dehydrogenases of the citrate cycle increasing the substrate availability of NADH to the respiratory chain that could lead to an increase in mitochondrial respiration. On the other hand, in a fecal model of peritonitis in pigs, Vuda and colleagues (25) did not find that NE improved mitochondrial function when they measured the in vitro effect of NE on respiratory efficiency of complex I and complex II of hepatic cells taken after prolonged exposure to sepsis.

Although the present study does not elucidate the mechanism by which NE reversed mitochondrial dysfunction in the NE treatment group, we found that NE caused an increase in $DO_2$ (organ oxygen delivery) in the NE septic group as compared with the septic control group (Table 1). In a previous study, we showed that NE maintained hepatic blood flow as compared to an untreated septic group in a similar canine model (3), while NE would have increased oxygen delivery to the liver in the present study by increasing blood Hb concentration. Alpha agonists such as NE, have been shown to cause splenic contraction and thereby to promote auto-transfusion in previous sepsis studies (3). In this case, NE may have reversed any contribution of ischemic hypoxia to the mitochondria reducing mitochondrial oxidant damage. Mitochondria are the major sources of intracellular reactive oxygen species (ROS) in a resting cell and a major target of these species (7, 8, 9). Under normal circumstances, complex interacting antioxidant defense systems control oxidative stress within mitochondria, but this may not be the case in SS. Significantly, although this study does not delineate the mechanism involved, the fact that NE can reverse mitochondrial dysfunction in SS provides a rationale for its use in the treatment in the clinical situation. Whether other vasopressors would provide a similar beneficial effect on mitochondrial function is not clear at this time.

Nevertheless, despite the fact that NE resulted in an improvement in maximal OCR in the NE group, we found that this effect did not lead to an attenuation of LA. In the NE septic group, mean blood lactate concentration increased over the course of the study, such that at the 5 hr measurement period, lactate was not different from that observed in the septic control group. Since parameters of mitochondria' respiration were not different between the NE septic group and the non-septic control group, this highlights the important clinical observation that while mitochondrial dysfunction could contribute to LA in sepsis in conditions in which MAP decreases to a low enough value to cause mitochondrial hypoxia, it is nevertheless possible for LA to develop despite the fact that mitochondrial function may be normal.

In contrast to NE treatment, we found that GSS was capable of improving the three most important parameters measured in this study, namely MAP, mitochondrial dysfunction and LA. GSS contains two hydroxyl moieties attached to the benzoic acid ring (2,5-dihydroxybenzoic acid sodium salt) and is a breakdown product of aspirin (21, 24) (FIG. 2A). GSS has potent antioxidant properties that might account for its greater beneficial effect than NE on mitochondrial function in this model. In the present study, not only did GSS increase maximal OCR as compared with the septic control group, but GSS caused a marked increase in coupled respiration and increased basal respiration. Although GSS only tended to increase mitochondrial complex IV by enzymatic measurements, we think that measurements of OCR by the Seahorse Instrument provide a much more sensitive indication of mitochondrial function than does the assessment of mitochondrial enzymatic activity of the different complexes. The Seahorse Instrument gives an overall functional assessment of the entire electron transport chain in which the functionality of the whole chain is assessed, while the significance of small reductions in enzymatic activity of the different complexes in terms of their role in reducing OCR may be difficult to assess. The mechanism by which GSS enhanced mitochondrial function was most likely related to GSS's antioxidant effects that led to an increase in coupled respiration by enhanced transfer of ATP out of the cell by adenine nucleotide translocase (FIG. 1). Since there would be less feedback inhibition of respiration by ATP, mitochondrial coupled respiration would be higher in the gentisic septic group.

Figure 2:
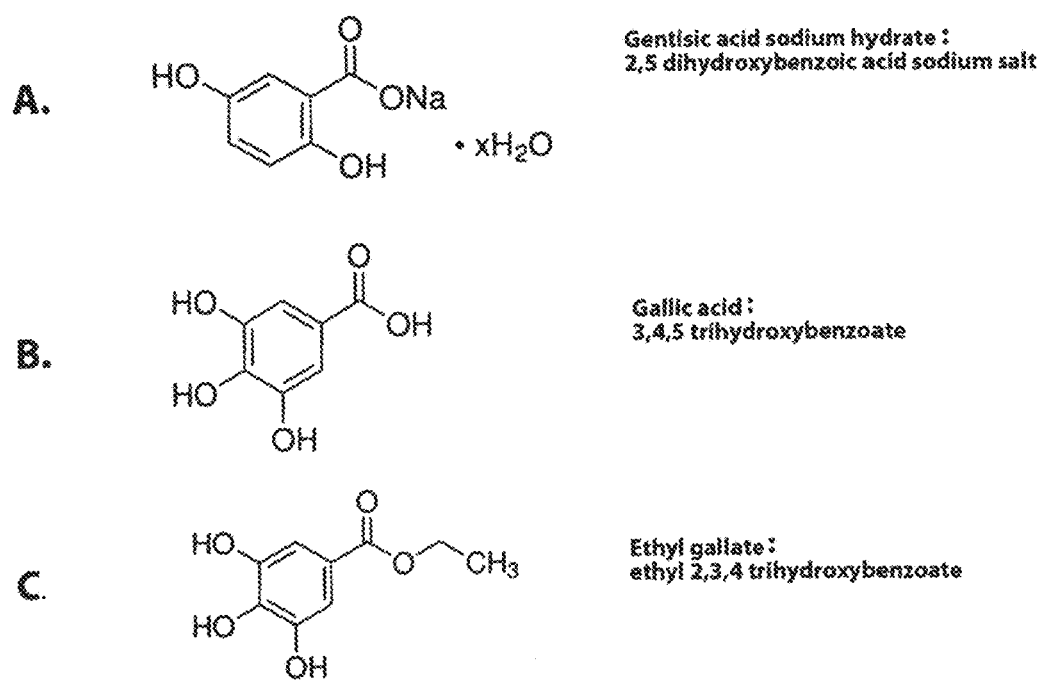
FIG. 2. In canine models of septic shock, phenolic compounds of very similar structure produce markedly different physiological effects.

We also demonstrated that in the septic group, GSS caused a reduction of LA as compared with septic control group and as compared with the NE septic group. We do not believe that this effect of GSS on LA was only a consequence of its ability to improve mitochondrial function, since NE treatment in the NE septic group also caused a return in mitochondrial function to non-septic control values without having this effect on LA. While not wishing to be bound to a particular hypothesis, we consider some possibilities as follows. In one case, the mechanism of GSS's effect could be related to a decrease in splanchnic production of lactate, since we found that lactate production increased from the splanchnic organs in previous experiments in a similar model (3). On the other hand, GSS could reduce lactate concentrations within the hepatic cytosol by mechanisms independent of mitochondrial function (FIG. 2). For instance, this could occur by enhancing hepatic gluconeogenesis by means of the Cori cycle, which by utilizing lactate from the cytosol pool, could allow for greater influx of lactate from the blood, or by reducing glycolysis which in turn could lessen hepatic lactate production. Both mechanisms have been identified as being important to lactate metabolism in different diseases. For instance, in asthma, β-agonist effects have been shown to produce elevations in lactate by glycolysis in conditions in which there is normal tissue perfusion, and it is known that sepsis is a β-hyperadrenergic state (29). On the other hand, in diabetes, metformin has been shown to suppress gluconeogenesis by inhibiting mitochondrial glycerophosphate, leading to the development of LA (30), while the finding of LA in sepsis may be attributable to a similar mechanism. The extent to which each of these mechanisms could play a role in GSS's effect is not yet clear, but is worthy of future investigation.

As part of this study, we also determined the effect of gallic acid on hepatic mitochondrial function and LA in this sepsis model. We chose gallic acid because we knew that gallic acid did not increase MAP in this model based on preliminary experiments and because it is also a potent antioxidant that is of similar structure to GSS (24). In this case, we wanted to assess whether an antioxidant without any effect on MAP could improve mitochondrial function and the development of LA in this model. While we found that gallic acid increased maximal respiration in a manner similar to NE, in contrast to the results found in the NE treatment group, we found that gallic acid caused a significant reduction in LA (Table 2). Thus, even though changes in mitochondrial function occurred to the same extent between gallic acid and NE treatments, the changes in LA were different between them. This observation would again provide further evidence that correction of LA in sepsis does not necessarily follow the correction of hepatic mitochondrial dysfunction, and that non-mitochondrial pathways may be involved in the development of LA in SS.

Nevertheless, unlike GSS, gallic acid did not increase coupled respiration in the septic animal, but did increase maximal respiration. The explanation for the different effects between GSS and gallic acid on mitochondrial function in SS is not yet clear, but many be related to the different physical properties of the two agents, since the water solubility and pKa are markedly different (24). The pKa of gallic acid is very acidic (i.e. pH=4.2 in unbuffered solution), and this could lower the pH of the hepatocyte relatively reducing the compound's antioxidant ability, while GSS is the salt of an acid and would have more of a basic effect with less lowering of intracellular pH (i.e. pH=8.2 in the unbuffered solution). Overall, these results indicate that despite comparable antioxidant capabilities, closely structured phenolic compounds may have markedly different biological properties.

Thus, in a canine model of SS, we found that hepatic mitochondrial dysfunction evolved over the course of sepsis in which the predominant effect observed was a reduction in maximal OCR. Although NE was able to reverse mitochondrial dysfunction in SS, this effect was not associated with an improvement in LA, so that mitochondrial dysfunction is not the sole prerequisite for the development of LA in sepsis. In addition, we found that GSS is a new treatment of SS. We showed that GSS produced an increase in MAP in which HR were lower than values found with NE treatment. Besides this, GSS reversed mitochondrial dysfunction and caused a reduction in LA. We speculate that GSS could reduce LA not only by normalizing mitochondrial function through its antioxidant properties, but may increase the hepatic cytosolic clearance of lactate, either by decreasing the rate of hepatic glycolysis or by increasing hepatic gluconeogenesis. We propose that GSS is a novel therapy for the treatment for LA and the development of cardiovascular collapse in SS.

The invention will now be further described by way of examples; however, the invention is not necessarily limited by the examples.

Results

Among the 5 initial treatment groups, the time to reach the septic condition from baseline was not different, measuring (mean±SD) 4.1±1.3 hrs (n=13) in the septic control group, 4.9±1.8 hrs (n=10) in the norepinephrine septic group, and 4.8±2.4 hrs (n=11) in the gentisic septic group. In the non-septic control group (n=16) and the GSS non septic group (n=5), we made measurements at 4.5 hrs post baseline in the sham-shock condition. In the 5 groups, there were no differences in the mean animal body weights, measuring 20.3±2.7 kgs in the septic control group, 20.7±1.7 kgs in the NE septic group, 22.3±2.4 kgs in the gentisic septic group, 21.1±2.7 kgs in the non-septic control group, and 23.6±1.9 kgs in the GSS control group. There were also no differences in the total amount of volume infused in the three septic groups over the course of the experiment, measuring 6±1 L in the septic control group, 6±1.6 L in the NE septic group, and 6.2±1.7 L in the gentisic septic group. On the other hand, we administered significantly less fluid in the non-septic groups (P<0.05) which measured 3.7±1 L in the non-septic and 3.4±0.6 L in the GSS non septic group. All animals in each of the 5 groups survived the last measurement condition.

Hemodynamic and Laboratory Results

Figure 3:
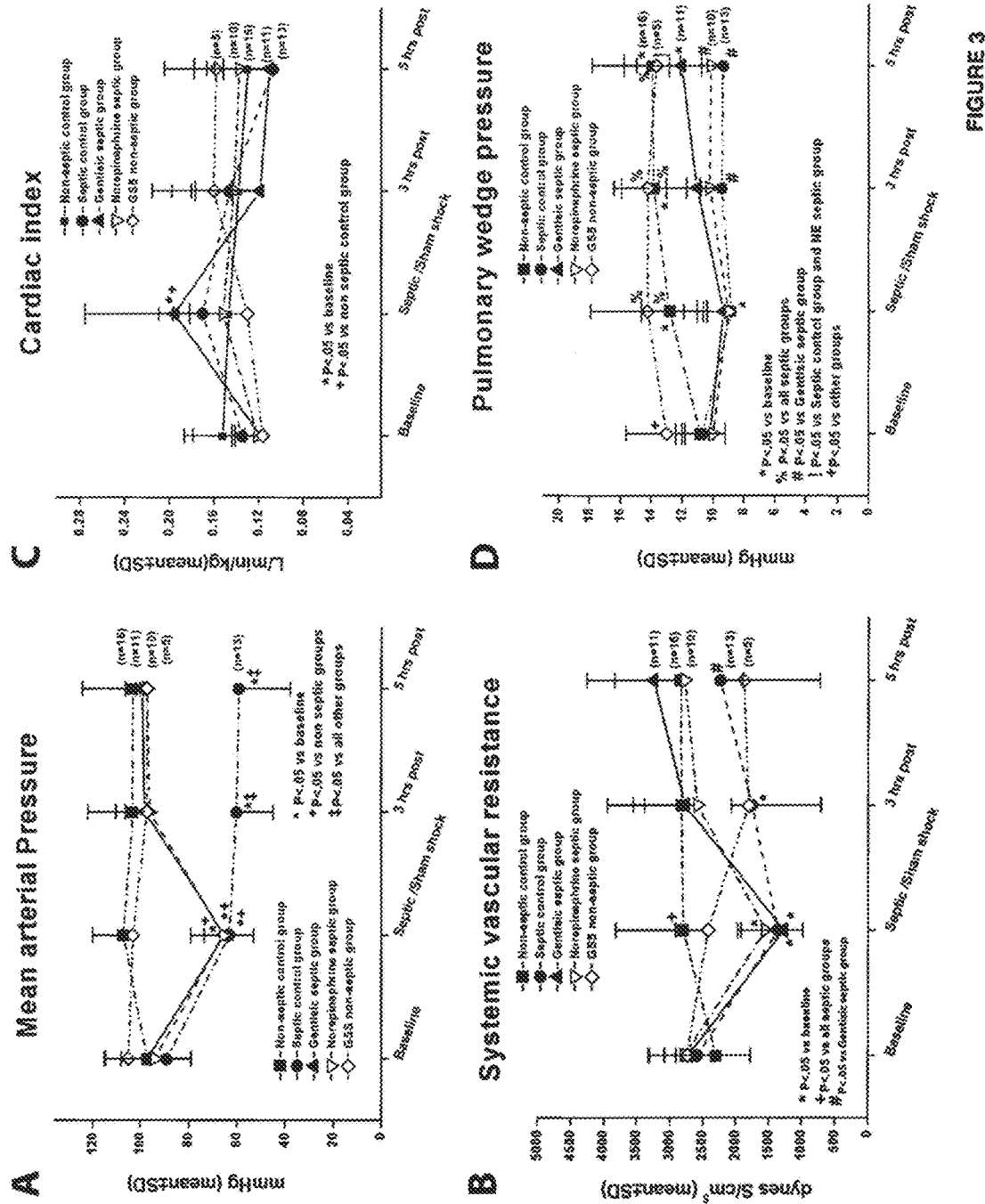
FIG. 3. This figure shows select hemodynamic parameters for the 5 initial in vivo groups over the four measurement periods. In panel A, in the three septic groups, mean arterial pressure (MAP) in the septic shock condition decreased to approximately 60% of baseline. In the gentisic septic group and the norepinephrine (NE) septic group, both treatments increased MAP back to the baseline value. In panel B, systemic vascular resistance (SVR) decreased in the three septic groups. In the gentisic septic group and the NE septic group, both treatments increased SVR back to the baseline value. In panel C, cardiac outputs were similar among all of the groups over the posttreatment conditions. In panel D, there were only small differences in pulmonary wedge pressures among the groups. GSS is gentisic acid sodium salt. Statistical analyses included two-way repeated measures ANOVA and SNK multiple comparison test.
Figure 4:
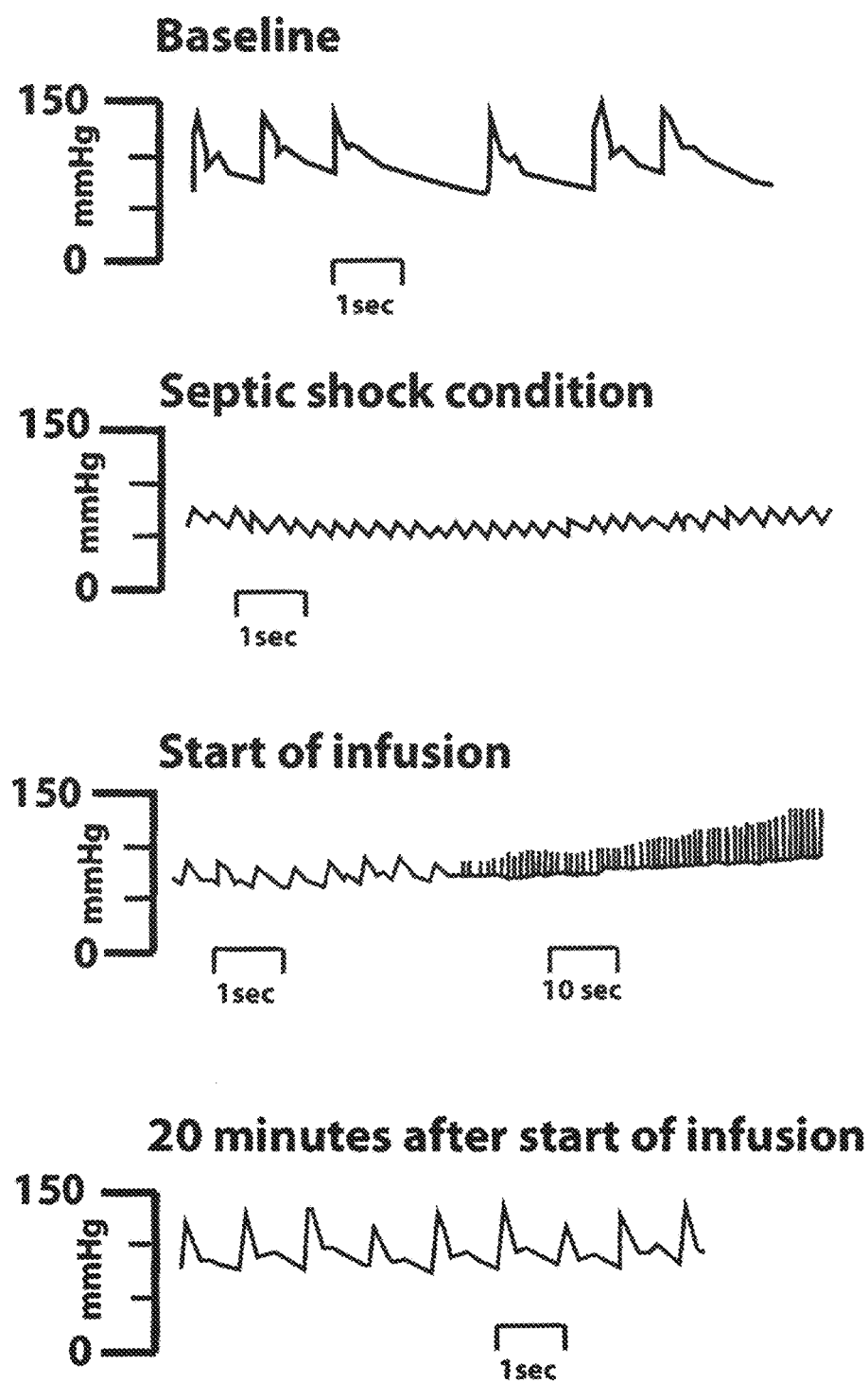
FIG. 4. Systemic blood pressure is shown for a dog in the gentisic septic group in the different conditions. Gentisic acid sodium salt produced an increase in blood pressure within a few minutes of infusion that reached the baseline value after approximately 20 minutes of infusion.

At baseline, there were no differences in MAP among the 5 groups which averaged around 100 mmHg (FIG. 3A). In the two non-septic groups, MAP remained at this baseline value for the remainder of the study, while in 3 septic groups, mean MAP decreased to approximately 60 mmHg at the septic shock condition. In the septic control group, MAP remained at this low value for the duration of the experiment. On the other hand, in both the NE and gentisic septic groups, treatments caused a return in MAP to baseline where MAP remained for the 3 hr post and 5 hr post treatment intervals. The increases observed with both treatments occurred within minutes of infusion, similar to the results we found in a previous study when we administered ethyl gallate in this septic model (19). We show an example of the increase in MAP that occurred in the gentisic septic group in FIG. 4. The average dose of NE infused over the 5 hr interval was 0.51±0.22 ug/kg/min. In the gentisic septic group, the average dose of GSS infused over the same interval was 0.55±0.29 mg/kg/min. The average infusion rate of GSS in the GSS non-septic group was 0.48±0.008 mg/kg/min.

In the septic shock condition, the mechanism for the reduction in MAP among the septic groups was due to a decrease in SVR (FIG. 3B). For the most part, CO remained relatively unchanged over the course of the study in the 5 groups (see FIG. 3C). In the gentisic septic group, although CO increased in the septic shock condition prior to GSS treatment, by the end of the study, CO were similar among the groups. In the NE septic and gentisic septic groups, both treatments caused an increase in SVR at 3 hrs and 5 hrs posttreatment as compared with the septic shock condition (see FIG. 3B). In the GSS non-septic group, although there was no significant change in SVR with treatment, SVR tended to decrease with this treatment over the course of the study. In the non-septic control group, there was little change in SVR over the different measurement intervals.

In this protocol, although we attempted to keep Pwp close to the baseline value, there were slight changes in Pwp observed over the course of the study in the 5 groups, particularly in the non-septic groups, since we needed to constantly infuse intravenous volume to administer the anesthetic agents in the latter groups. Overall, however, these changes were small (FIG. 3D).

Figure 5:
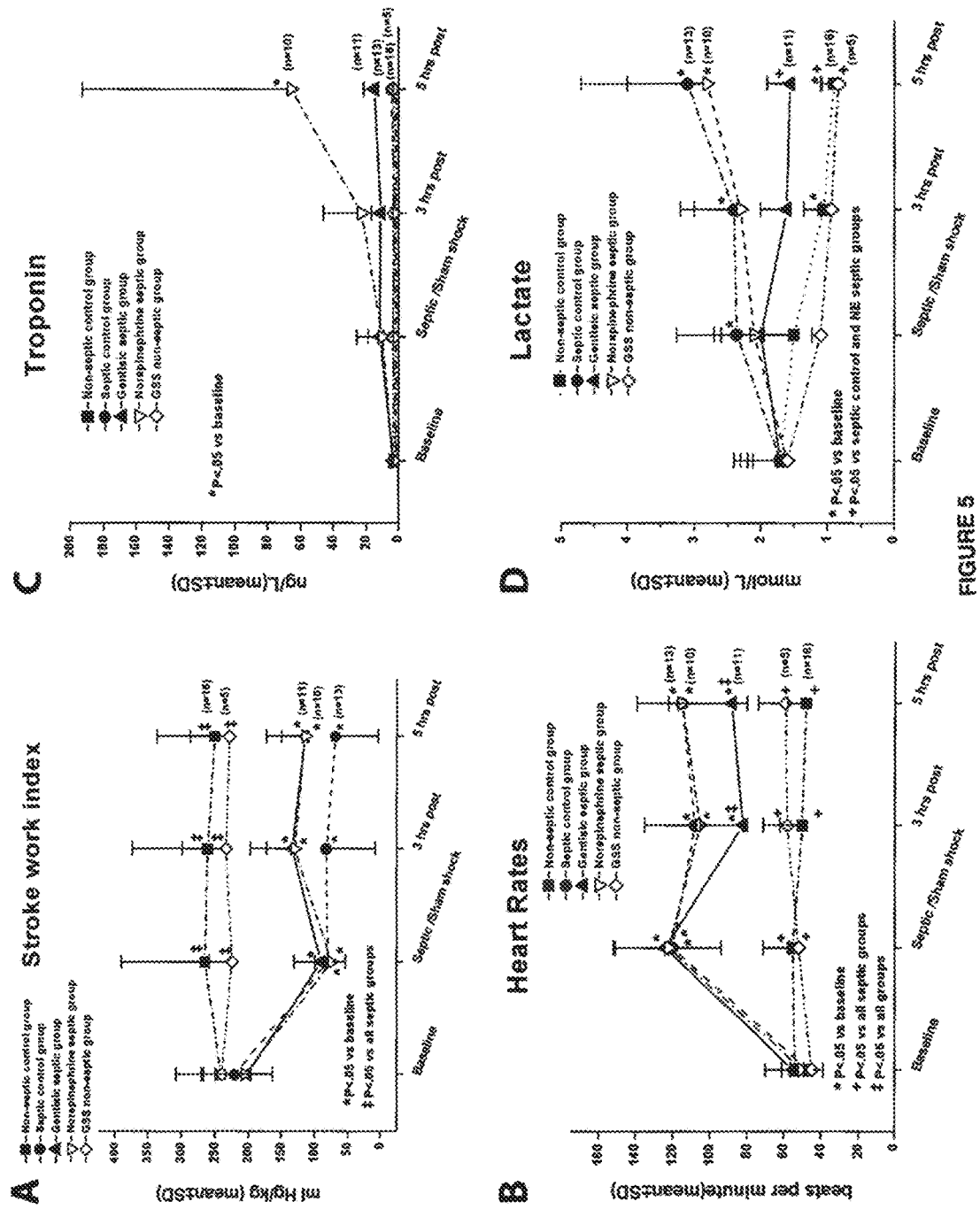
FIG. 5. This figure shows additional hemodynamic parameters for the 5 initial in vivo groups over the four measurement periods. In panel A, stroke work decreased in the septic groups over the course of the study, In the gentisic septic group and the norepinephrine (NE) septic group, both treatments caused an increase in stroke work, but the results were not significant among the septic groups. In panel B, heart rates increased in the septic groups over the course of the study. In the gentisic septic group, heart rates were lower at 3 hr and 5 hr posttreatment conditions as compared with the other septic groups. In panel C, troponin, our index of myocardial injury, increased in the NE septic group, while it did not change in the other groups. In panel D, serum lactate increased in the NE septic group and the septic control group over the course of study, while it decreased in the non-septic groups and did not change in the gentisic septic group. GSS is gentisic acid sodium salt. Statistical analyses included two-way repeated measures ANOVA and SNK multiple comparison test.

In the three septic groups, we also observed that there were marked decreases in the stroke-work index over the course of the study as compared with the non-septic groups (FIG. 5A). In the NE septic and gentisic septic groups, both treatments caused an increase in stroke work index as compared to the septic control group at the 3 hr and 5 hr intervals, but these values did not reach statistical significance among the groups. In addition, we found that HR increased in the three septic groups during bacterial infusion from a mean of about 60 bpm at baseline to about 120 bpm at the septic shock condition (FIG. 5B). In the gentisic septic group, this treatment caused a significant decrease in HR at 3 hrs and 5 hrs posttreatment as compared with the other septic groups. As well, we found that troponin, our index of myocardial injury, increased in the NE septic group at the 5 hr interval, while we did not observe this finding in the other septic groups (FIG. 5C).

The changes in blood lactate differed among the 5 groups (FIG. 5D). In the two non-septic groups, there was a progressive decline in blood lactate concentrations over the course of the study. On the other hand, blood lactate concentrations significantly increased in the septic control group and the NE septic group toward the end of the study, while blood lactate concentrations did not increase and even tended to decrease slightly in the gentisic septic group.

To determine the extent to which oxygen delivery might have affected the changes in lactate concentrations with the different treatments, we also calculated $DO_2$ in the 5 groups (Table 1). We found that on the mean $DO_2$ was lowest in the septic control group. In the NE septic group, NE treatment caused an increase in $DO_2$ as compared with the septic control group and the gentisic septic group (Table 1). In terms of the latter effect, because CO (FIG. 3C) and $PO_2$ (approximately 400 mmHg in each group) were not different among the groups, we subsequently determined that the mechanism for the increase in $DO_2$ with NE treatment was due to an increase in Hb which, as compared with the other groups, increased at 3 hrs and 5 hrs posttreatment in this group (Tables 3 to 8). Mixed venous $PO_2$ were not different among the groups, while pH at the end of the study was higher in the gentisic septic group (Tables 3 to 8). Changes in other parameters among the groups were small (Tables 3 to 8).

There were also no differences in hepatic MCT1 protein among the groups in which MCT1 measured 30±28 pg/mg tissue in the septic control group, 25±20 pg/mg tissue in the non-septic control group. 38±8 pg/mg tissue in the GSS septic group, 17±26 pg/mg tissue in the norepinephrine group, 32±7 pq/mg tissue in the GSS non-septic group, and 25±6 pg/mg tissue in the gallic acid group.

Mitochondrial Measurements

Figure 6:
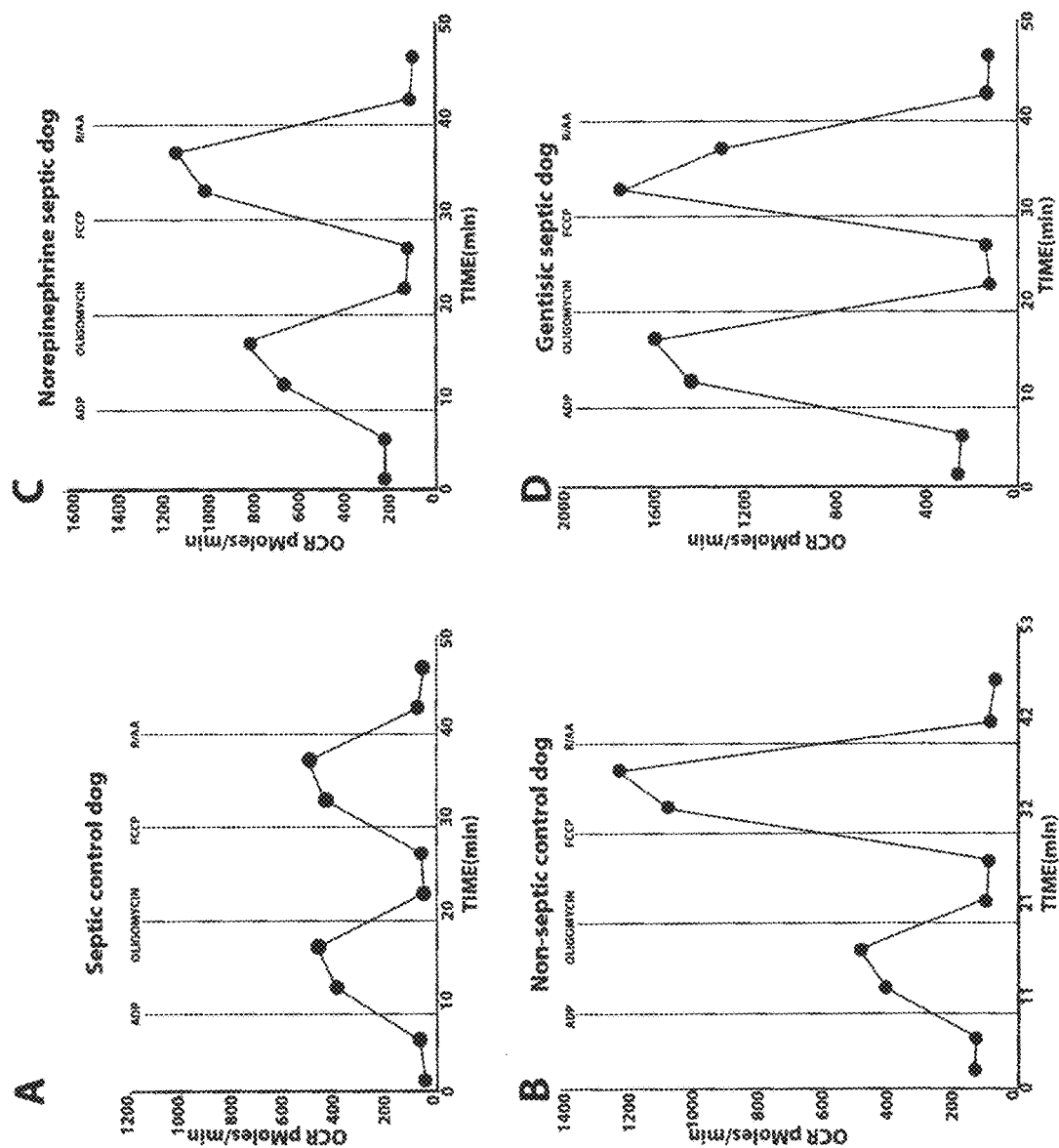
FIG. 6. Oxygen consumption rates (OCR) that we measured in the Seahorse Instrument are shown from mitochondria harvested from an animal in the septic control group (panel A), in a non-septic control dog (panel B), in the norepinephrine (NE) septic group (panel C), and in the gentisic septic group (panel D) under different metabolic conditions. In each experiment, we obtained two measurements in each condition that we averaged in the calculation of the mean data (see FIGS. 7 and 8), In panel A, basal OCR was slightly low in the animal in the septic control group as compared with the non-septic control group. When ADP was added to the preparation, OCR rate in the septic animal in panel A was not different from the animal in the non-septic control group (panel B). However, the response to FCCP (carbonyl cyanide p-trifluoromethoxy-phenylhydrazone) in the animal in the septic control group (panel A) was attenuated as compared with the animal in the non-septic control group (panel B). With norepinephrine treatment, there was a restoration in the response to FCCP in the NE septic group (panel C). In the animal in the gentisic septic group, there was a large response in OCR to ADP which nearly equaled the response to FCCP (panel D).

In the mitochondrial preparation, we found that the predominant effect of SS on oxygen consumption rates (OCR) was to cause a decrease in maximal respiration. We show examples of OCR under the different mitochondrial conditions for different groups in FIG. 6. In the septic control group (FIG. 6A), basal OCR was slightly less than values found in the other groups. Despite this, when we administered ADP to the preparation, we found that OCR in the septic control group increased to an extent not much different than that found in the non-septic control group (FIG. 6B). In contrast, when we added the protophore FCCP at 4 uM to the preparation, there was a large increase in OCR in the non-septic control group that was attenuated in the septic control group (FIG. 6A). In the NE septic group, the predominant effect of NE treatment was to restore the increase in OCR in response to FCCP (FIG. 6C), such that the effect of FCCP on OCR was now similar to that found in the non-septic control group. In the gentisic septic group (FIG. 6D), in addition to restoring basal respiration to the non-septic control value, GSS treatment produced a greater response to ADP as compared to the other groups. In this case, the OCR response with ADP was quite similar to that found with FCCP of 4 uM. In the GSS non-septic group, the results were very similar to those found in the non-septic control group, as discussed below.

Figure 7:
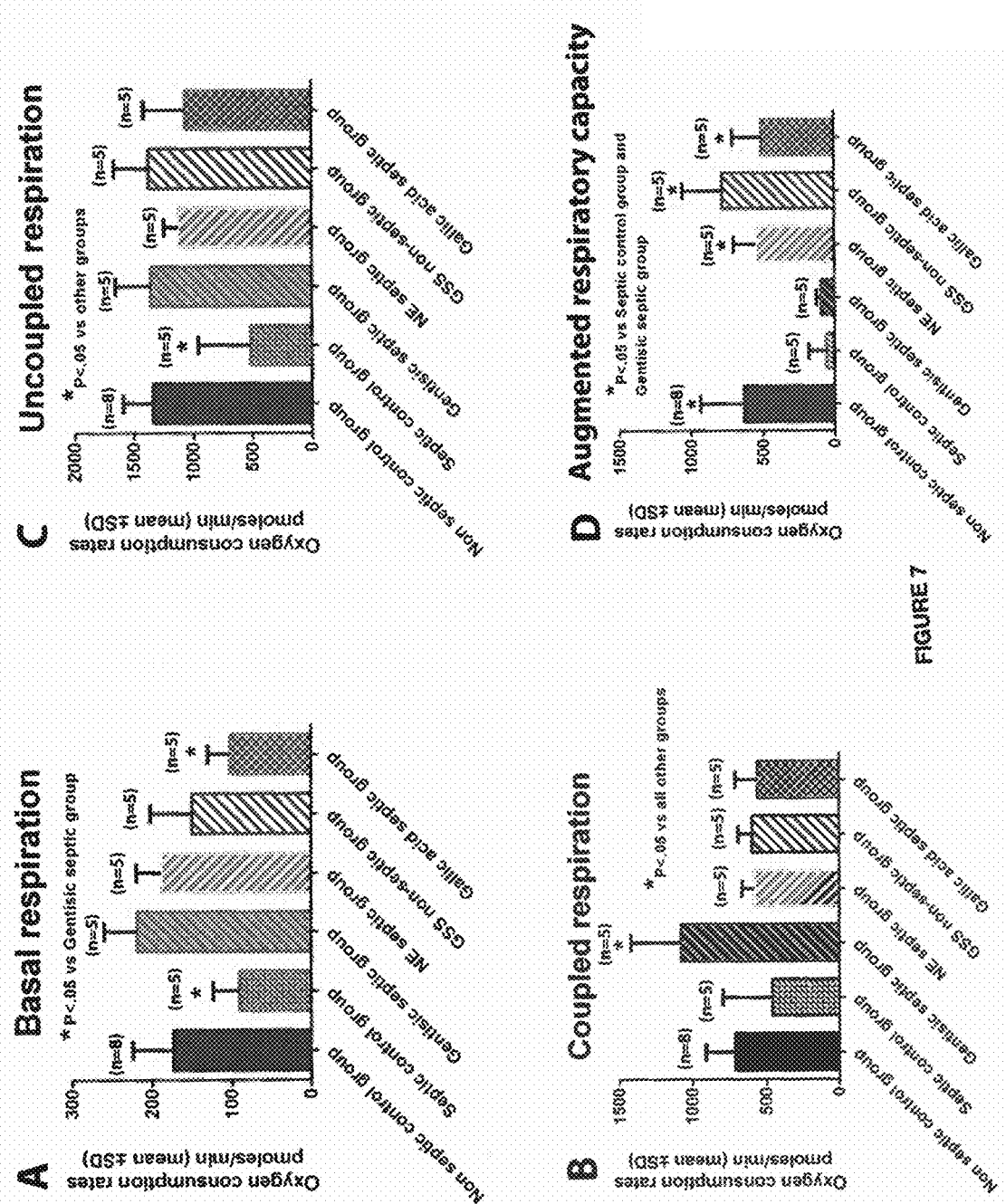
FIG. 7. Mean oxygen consumption rates (OCR) under the different metabolic conditions are shown for the five initial groups and the gallic acid septic group. In panel A, basal OCR in the septic control group was significantly less than that measured in the gentisic septic group. In panel B, coupled respiration in the gentisic septic group was significantly greater than the other groups. In panel C, uncoupled (maximal) OCR in the septic control group was lower as compared with the other groups in which we used a FCC of 4 uM (ie maximal) in the analysis. In panel D, augmented respiratory capacities were lowest in the septic control group and the gentisic septic group as compared with the other groups. Augmented respiratory capacity was calculated from the difference between uncoupled and coupled respiration (see text for discussion). Statistical analyses included one way randomized ANOVA and SNK multiple comparison test.
Figure 8:
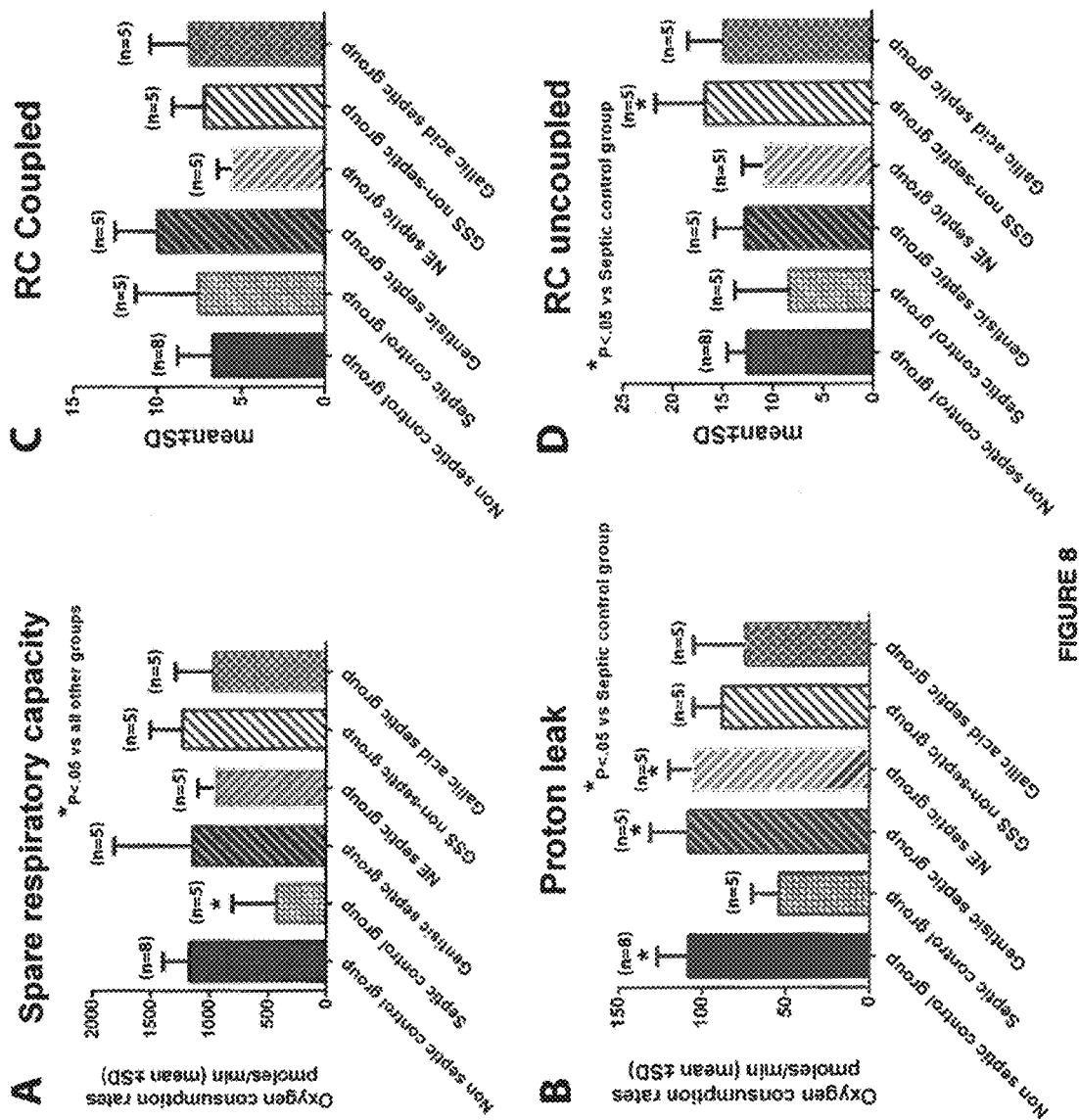
FIG. 8. Parameters derived from oxygen consumption rates (OCR) are shown for the five initial groups and the gallic acid septic group. In panel A, spare respiratory capacity in the septic control group was reduced as compared with the other groups. Spare respiratory capacity was derived from uncoupled respiration minus basal respiration. In panel B, the proton leak was determined from oligomycin insensitive OCR. Proton leak was reduced in the septic control group as compared with most of the other groups. In panels C and D, respiratory control ratios (RC) for coupled respiration and uncoupled respiration were not much different among the groups.

The mean results of mitochondrial OCR parameters are shown in FIGS. 7 and 8. In FIG. 7A, there was a decrease in basal respiration in the septic control group, particularly as compared with that found in the gentisic septic group. When we added ADP to the preparation to measure coupled respiration (state$_{ADP}$) (FIG. 6B), coupled respiration in the septic control group was not different from that found in the non-septic control group. However, in the gentisic septic group, there was a large increase in coupled respiration that was significantly greater than those measured in the other groups. The results obtained when we added FCCP at 4 uM to the preparation to achieve maximal (uncoupled) respiration are shown in FIG. 6C. In the septic control group, as compared with the other groups, there was a reduction in uncoupled respiration, while there was no difference in maximal OCR among the other groups.

In addition, we calculated the augmented respiratory capacity (FIG. 6D) as the difference between uncoupled and coupled respiration in the different groups. In the septic control group and the gentisic septic group, there was a reduction in augmented respiratory capacity as compared with the other groups. However, this occurred because of different mechanisms between the two groups. In the septic control group, there was a normal response to ADP, but a failure to increase OCR in response to FCCP, the net effect being a reduction in maximal respiration. On the other hand, in the gentisic septic group, there was a very large increase in OCR in response to ADP which equaled that found with FCCP, so that augmented respiratory capacity also decreased in the gentisic septic group. In addition, we calculated spare respiratory capacity from the difference between maximal and basal respiration. There was a significant reduction in spare respiratory capacity in the septic control group as compared with the other groups (FIG. 8A). We also measured the proton leak (FIG. 8B) from the OCR that could not be suppressed by oligomycin. There was a reduction in proton leak in the septic control group as compared with most of the other groups. Finally, we calculated respiratory control ratio, a measurement of efficiency of respiration, that was defined by the respective ratios of coupled respiration and uncoupled respiration over state oligomycin. In both cases, we found that there were only small differences among the groups (FIGS. 8C and 8D).

Moreover, we found that the enzymatic activity of mitochondrial complex IV significantly decreased in the septic control group (2.87±0.73 activity umol/min/mg protein) as compared with the non-septic control group (4.55±0.98 activity) ($P<0.01$), while the values in the gentisic septic group, NE septic group, GSS non septic group, and gallic acid septic group were not different and measured 3.68±0.59, 3.89±0.33, 3.01±0.66, and 2.44±0.63, respectively. These results were not different among the groups.

Gallic Acid Experiments

We found that unlike GSS treatment, gallic acid did not produce an increase in MAP in this model or any beneficial changes in hemodynamics (Table 2). In effect, the hemodynamic results obtained in the gallic acid septic group were very similar to those we observed in the septic control group. Despite the lack of hemodynamic changes, however, gallic acid treatment resulted in a reduction in lactate at 3 hrs and 5 hrs posttreatment that was comparable to those measured in the gentistic septic group (Table 2).

Gallic acid treatment also led to an improvement in mitochondrial function. Gallic acid restored the reduction in maximal respiration that was otherwise observed in the septic control group, while coupled respiration and maximal respiration were not different from values found in the non-septic control group (FIGS. 7 and 8).

Methods

The University Animal Care Committee approved these canine experiments which conform with the Guide for the Care and Use of Laboratory Animals published by the US National Institutes of Health (NIH Publication No 85-23, 1996) (22).

Animal Preparation

We used a bacteremic model of *Pseudomonas aeruginosa* in this study as previously described (20). We used this particular model, since we wanted to measure mitochondrial function and LA under conditions of an acute and intensive inflammatory response analogous to that which would occur in a severe bout of SS in the clinical condition. In this regard, we infused the bacteria ($\sim 10^{10}$ colony forming units/hour of *P. aeruginosa* ATCC 27853) mixed in normal saline solution over the duration of the study, while in the non-septic groups, we administered normal saline solution as a placebo over a similar time frame (see groups below). Over the course of the experiment, we studied the animals (18 to 26 kg) while anesthetized with sufentanil citrate (0.05-0.3 ug/kg/min) and midazolam (5 ug/kg/min), and while being ventilated receiving 100% oxygen to maintain arterial around $PO_2 \sim 400$ mmHg. We adjusted the ventilator rate over the course of the study to attenuate the development of the metabolic acidosis that is usually observed (20).

To assess hemodynamics in this model, we inserted vascular catheters under sterile conditions as previously described (20), after which we connected the catheters to pressure transducers (Cobe, Argon) that were referenced relative to the left atrium and connected to a chart recorder (Astro-Med, W Warwick, R.I.). To measure MAP, we inserted a polyethylene catheter into the right femoral artery, while to measure pulmonary vascular pressures, we inserted a Swanz-Ganz catheter (Edwards Lifesciences, Irvine, Calif.) by percutaneous techniques through the right jugular vein. From the Swanz-Ganz catheter, we obtained measurements of pulmonary arterial pressure (Ppa), wedge pressure (Pwp), and right atrial pressure (Rap), as well as determinations of thermodilution cardiac output (CO).

From the hemodynamic measurements, we calculated SV from CO/heart rates (HR), stroke work (SW) from [SV*(MAP−Pwp)], and systemic vascular resistance (SVR) from [(MAP-Rap)/CO)*80]. We also normalized measurements of SV, SW, and CO and organ oxygen delivery ($DO_2$) to body weight. We calculated $DO_2$ from CO×Hb×1.34 ml oxygen per gram of Hb, since Hb was 100% saturated at a $PO_2$ of ~400 mmHg. From the arterial catheter and distal port of the Swanz-Ganz catheter, we also took arterial and mixed venous blood samples, respectively, for analyses of $PO_2$, $PCO_2$, and pH.

In addition, we placed another polyethylene catheter into the left jugular vein, also by percutaneous techniques, for infusion of the bacteria and intravenous fluids and for obtaining blood chemistry and hematological samples. Since the baseline Pwp found in this model usually averages≈8-10 mmHg, we infused normal saline solution as necessary to maintain Pwp relatively constant over the duration of this study. In each condition (see further below), moreover, we obtained blood samples for measurements that included among others serum electrolytes, creatinine, blood urea nitrogen (BUN), liver function tests, troponin, our index of myocardial damage, lactate concentrations, hematocrit (Hct) and WBC. From continuous collections of urine, we determined urine volume and urine creatinine and calculated creatinine clearance as previously described (20). The Clinical Chemistry Laboratory at the Health Sciences Centre performed the clinical laboratory tests.

Experimental Protocols

We included 5 groups of animals in the initial phase of this study. These groups included a septic control group, a non-septic control group, a norepinephrine (NE) septic group, a gentisic acid sodium salt (GSS) septic group, and a GSS non-septic group. In each group, we made baseline measurements of hemodynamics and blood parameters after approximately 1 hr period of stability. In the septic groups, after initiation of the bacterial infusion, we repeated the measurements in the septic shock condition. We defined the septic shock condition as the interval at which MAP decreased to 60-65 mmHg, since this would mark the MAP at which vasopressors would often be started in the clinical condition (18). While the bacteria were still being administered, we started an infusion of NE in the NE septic group to return MAP to the ~baseline value, while in an identical manner, we infused GSS in the gentisic septic group to maintain MAP comparable to the baseline value. In the septic control group, after the SS condition, we started an infusion of 5% dextrose in water ($D_5W$) at approximately 40 ml/hr for the remainder of the study, since D5W was the diluent for both the NE and GSS treatments.

In the two non-septic groups, since the septic shock condition usually occurred≈4.5 hrs after the start of bacterial infusion, we made measurements at comparable baseline and sham shock intervals in these groups. After the sham shock condition, we infused GSS mixed in D5W in the GSS non-septic group and infused $D_5W$ alone in the non-septic control group for the remainder of the study. In the GSS non septic group, we infused the GSS treatment at a comparable rate to that administered in the gentisic septic group.

In all groups, we then made posttreatment measurements at 3 hrs and 5 hrs after completion of the septic shock/sham-shock determinations.

Mitochondrial Preparation

After completion of the in-vivo measurements, we administered sodium pentobarbital (110 mg/kg) to euthanize the animal. In a subset of animals of each group, we immediately harvested a piece of liver and isolated the mitochondria as described by Schnaitman and Greenawalt (23). Briefly, we minced the extracted liver in mitochondrial isolation buffer (MSHE) that includes 70 mM sucrose, 210 mM mannitol, 5 mM HEPES, 1 mM EGTA, and fatty acid free bovine serum albumin (BSA). We then disrupted the tissue using a drill-driven glass/Teflon dounce homogenizer. We centrifuged the homogenate three times, after which we re-suspended the final pellet in a minimal volume of MSHE+BSA and determined protein (mg/ml). We diluted the mitochondrial preparation in cold mitochondrial assay solution (MAS) that contained 70 mM sucrose, 220 mM mannitol, 10 mM $KH_2PO_4$, 5 mM $MgCl_2$, 2 mM HEPES, 1 mM EGTA, and BSA for plating directly onto the custom Seahorse 24-well culture dish (~20 ug mitochondrial protein/50 ul per well; see further below). After centrifugation of the plate and addition of appropriate substrates, we viewed the mitochondria under a microscope to ensure consistent adherence to the well. We then transferred the plate to the XF24 Analyzer for initiation of the protocol as described below (17).

Mitochondrial Measurement of Oxygen Consumption Rates (OCR)

To examine mitochondrial function in this model, we used a novel new technology that is capable of measuring dynamic changes in mitochondrial function, not easily attainable by other technologies (17). The Seahorse® XF24 extracellular flux analyser (Seahorse Bioscience, MA, USA) refines the technology by which mitochondrial oxygen consumption can be measured. This technology uses a piston to reversibly enclose a small volume (7 ul) above the mitochondria that can monitor oxygen uptake in that volume for 2-5 min, then raises the piston, allowing the bulk incubation medium (~1 ml) to re-equilibrate. The ability to make up to 4 additions during the experiment allows mitochondrial respiration to be measured under various metabolic conditions. This piece of equipment has never been used to measure mitochondrial function in SS.

In this protocol, we sequentially measured mitochondrial function under various metabolic conditions (17). To obtain basal OCR, we first added a substrate to the preparation that contained pyruvate (10 mM) and malate (2 mM). We then added ADP (adenosine-diphosphate; 4 mM) that allows ATP synthase to function, producing an increase in OCR (coupled OCR) that is termed "$state_{3ADP}$". When the ATP/ADP ratio approaches equilibrium, pmf rises, after which proton reentry through the synthase stops and respiration slows. We terminated coupled respiration (i.e. $state_{3ADP}$) by the addition of the ATP synthase inhibitor oligomycin (2.0 uM) in which we achieved "$state_{oligomycin}$" where ATP recycling cannot contribute and there is a stable decrease in OCR. We then added the protonophore, FCCP (4 uM; carbonyl cyanide p-trifluoromethoxy-phenylhydrazone). FCCP leads to uncoupled respiration in which we previously titrated the concentration of FCCP to yield a maximal effect. In mitochondria in which ATP synthase activity is a limiting factor, uncoupled respiration may be greater than coupled respiration. This indicates that the mitochondria have reached maximal respiration in uncoupled respiration in which this respiration is not limited by ATP synthase activity (ie ATP accumulation feedbacks on OCR inhibition). We finally added rotenone (R; 2 uM) and antimycin A (AA; 2 uM) which are inhibitors of the electron transport chain (ETC) complexes, I and III, respectively. When added to the mitochondrial preparation, these inhibitors produce a marked decline in mitochondrial respiration since the electron transport chain is inhibited.

With each treatment group, we obtained measurements of basal OCR, coupled OCR (i.e. $state_{3ADP}$), and maximal OCR. In addition, we calculated coupled and uncoupled respiratory control ratios from $state_{3ADP}/state_{oligomycin}$ and uncoupled respiration/state $FCCP/state_{oligomycin}$, respectively. We determined spare respiratory capacity from [uncoupled respiration minus basal OCR), augmented respiratory capacity from (uncoupled respiration minus coupled respiration), and proton leak from oligomycin-insensitive OCR.

Determination of Enzymatic Activity of Mitochondrial Complex IV (Cytochrome c Oxidase)

As part of our assessment of mitochondrial function, we also measured the enzymatic activity of hepatic mitochondrial complex IV based on the rationale of Levy et al (10), since these investigators considered that dysfunction of complex IV was the most important determinant of abnormal mitochondrial function in SS. We determined complex IV activity spectrophotometrically by a temperature-controlled Ultrospec™ 2100 ultraviolet-visible spectrophotometer (Biopharmacia Biotech, Uppsala, Sweden) (17). Complex IV activity was measured at 25° C. by monitoring the absorbance decrease of reduced cytochrome c at 550 nm. The reaction was started by addition of 40 µmol/l reduced cytochrome c into 50 mmol/l phosphate buffer containing 2.5 pg mitochondrial protein solubilized with 0.02% laurylmaltoside.

To Determine Whether MCT1 Protein is Altered in Septic Shock

We also determined whether there were alterations in hepatic MCT1 protein in our septic shock model and whether any of the treatments administered in this study would affect hepatic MCT1 protein concentrations to alter lactate transport. We measured MCT1 from liver samples after obtaining the specimens from the euthanized animal. Canine MCT1 has marked homology of >80% with that of the human protein. We measured the MCT1 protein according to the instructions of the manufacturer (ab93048-rapbit polyclonal to monocarboxylic acid transporter 1, HRP conjugation Kit ab ab102890, human monocarboxylic acid transporter 1 full length protein ab152689, Abcam, Inc Toronto Ontario).

Gallic Acid Septic Group

In the gentisic septic group, the results showed (see further below) that GSS treatment improved MAP, mitochondrial function and attenuated the development of LA in our model. Nevertheless, because GSS also caused an increase in MAP, we wanted to know whether it was possible for a similar type of phenol compound to improve LA and mitochondrial dysfunction in our model without the necessity of increasing MAP, since the latter may affect blood flow to the liver (3). To address this possibility, we found in preliminary experiments that gallic acid may have these unique properties. Gallic acid is a phenolic compound that is found in wine and other foods that contains three hydroxyl groups joined to the benzoic acid structure (i.e. 3,4,5 trihydroxybenzoic acid) (FIG. 2B) (24). In this supplemental study, we examined the effect of gallic acid on hemodynamics and mitochondrial function in our *Pseudomonas aeruginosa* model in a manner identical to that described for GSS treatment.

Statistics

For the hemodynamic measurements determined in the 5 treatment groups and supplemental gallic acid group, we used a two-way ANOVA (split-plot) in which we normalized hemodynamic data (SV, CO, and SW) to body weight. In this statistical analysis, there were six groups of animals (i.e. 6 levels of A comparison) and 4 different time periods (4 levels of B comparison: i.e. baseline, septic shock condition and 3 and 5 hrs posttreatment GB-Stat V8, Dynamic Microsystems, Inc., Silver Springs, Md.). From the results of the ANOVA tables, we used a Student Newman Keuls' (SNK) comparison test to determine where there were differences observed among the groups at the specific time periods. In other analyses, when there was only one level of the B comparison present, we used a one way randomized ANOVA and SNK. We used two tail tests with significance of $P<0.05$. Results are reported as mean±1 SD.

The scope of the claims should not be limited by the preferred embodiments set forth in the examples, but should be given the broadest interpretation consistent with the description as a whole.

REFERENCES

1. Gutierrez G, Wulf M E: Lactic acidosis in sepsis: a commentary. *Intensive Care Med* 22: 6-16, 1996.
2. Vernon C, LeTourneau J L: Lactic Acidosis: recognition, kinetics, and associated prognosis. *Critical Care Clin* 26: 255-283, 2010.
3. Chrusch, C, Bands C, Bose D, Li X, Jacobs H, Duke K, Bautista E, Light R B, Mink S N: Impaired hepatic extraction and increased splanchnic production contribute to lactic acidosis in canine sepsis. *Am J Respir Crit Care Med* 161:517-526, 2000.
4. Poole R C, Halestrap A P: Transport of lactate and other monocarboxylates across mammalian plasma membranes. *Am J Physiol:* 264 (*Cell Physiol* 33); C761-C782, 1993.
5. Halestrap A P, and Wilson M C: The Monocarboxylate Transporter Family-Role and Regulation. *Life* 64: 109-119, 2112.
6. Halestrap A P: Monocarboxylic acid transport. *Compr Physiol* 3:1611-1643, 2013.
7. Galley H F: Bench-to-bedside review: Targeting antioxidants to mitochondria in sepsis. *Critical Care* 14: 230, 2010.
8. Galley H F: Oxidative stress and mitochondrial dysfunction in sepsis. *British Journal of Anaesthesia* 107: 57-64, 2011.
9. Grouser E D: Mitochondrial dysfunction in septic shock and multiple organ dysfunction syndrome. *Mitochondrion* 4: 729-741, 2004.
10. Levy R J, Deutschman C S: Cytochrome c oxidase dysfunction in sepsis. *Crit Care Med* 35: S468-S475, 2007.

11. Muravchick S, Levy R J: Clinical implications of mitochondrial dysfunction. *Anesthesiology* 105: 819-837, 2006.
12. Brand M D, and Nicholls D G: Assessing mitochondrial dysfunction in cells. *Biochem J* 435: 297-312, 2011.
13. Barrientos A, Fontanes F, Diaz F: Evaluation of the mitochondrial respiratory chain and oxidative phosphorylation system using polarography and spectrophotometric enzyme assays. *Curr Protoc Hum Genet.* 2009 October; Chapter 19: Unit 19.3. doi: 10.1002/0471142905.hg1903s63
14. Brealey D, Brand M, Hargreaves I, Healtes S, Land J, Smolenski R, Davies N A, Cooper C E, Singer M. Singer M: Association between mitochondrial dysfunction and severity and outcome of septic shock. *Lancet* 360: 219-223, 2002.
15. Japiassu A M, Paula A, Santiago A, d'Vila Joana da Costa P, Garcia-Soua Luiz F, Galina A, Farla-Neto Hugo C Casto, Bozza F A, Oliveira M F: Bioenergetic failure of human peripheral blood monocytes in patients with septic shock is mediated by reduced F1Fo adenosine-5-triphosphate synthase activity. *Crit Care Med* 39: 1056-1063, 2011.
16. Jeger V, Djafarazadeh S, Jakob S M, Takala J: Mitochondrial function in sepsis. *Eur J Clin Invest* 43: 532-542, 2013.
17. Roy Chowdhury S K, Smith D R, Saleh A, Schapansky J, Marquez A, Gomes S, Akude E, Morrow D, Calcutt N A, Fernyhough P: Impaired adenosine monophosphate-activated protein kinase signalling in dorsal root ganglia neurons is linked to mitochondrial dysfunction and peripheral neuropathy in diabetes. *Brain* 135:1751-66, 2012.
18. Dellinger R P, Levy M M, Rhodes A, Annane D, Gerlach H, Opal S M, Sevransky J E, Sprung C L, Douglas I S, Jaeschke R, Osborn T M, Nunnally M E, Townsend S R, Reinhart K, Kleinpell R M, Angus D C, Deutschman C S, Machado F R, Rubenfeld G D, Webb S A, Beale R J, Vincent J L, Moreno R; Surviving Sepsis Campaign Guidelines Committee including the Pediatric Subgroup: Surviving sepsis campaign: international guidelines for management of severe sepsis and septic shock: 2012. *Crit Care Med* 41: 580-637, 2013.
19. Mink S N, Jacobs H, Gotes J, Kasian K, Cheng Z Q: Ethyl gallate, a scavenger of hydrogen peroxide that inhibits lysozyme-induced hydrogen peroxide signaling in vitro, reverses hypotension in canine septic shock. *J Appl Physiol* 110: 359-374, 2011.
20. Gotes, J, Jacobs, Kasian K, Cheng Z Q, Mink S N: Benefits of ethyl gallate vs norepinephrine in the treatment cardiovascular collapse in *Pseudomonas aeruginosa* septic shock in dogs. *Crit Care Med* 40: 560-572, 2012.
21. Hutt A J, Caldwell J, Smith R L: The metabolism of [carboxyl-14C] aspirin in man. *Xenobiotica* 12:601-10, 1982.
22. National Institutes of Health. Guide for the Care and Use of Laboratory Animals (1996) Bethesda, Md., National Institutes of Health, (*NIH Publication* No 85-23).
23. Schnaitman C, Greenawalt J W: Enzymatic properties of the inner and outer membranes of rat liver mitochondria. *J Cell Biol* 38:158-75, 1968.
24. Sroka Z, Cisowski W: Hydrogen peroxide scavenging, antioxidant and anti radical activity of some phenolic acids. *Food and Chemical Toxicology* 41: 753-758, 2003.
25. Vuda M, Brander L, Schroder R, Jakob S, Takala J, Djafarzadeh S: Effects of catecholamines on hepatic and skeletal muscle mitochondrial respiration after prolonged exposure to faecal peritonitis in pigs. *Innate Immunity* 18: 217-230, 2011.
26. Gellerich F N, Trumbeckaite S, Opalka J R, Gellerich J F, Chen Y, Neuhof C, Redl H, Weerdan K, Zierz S: Mitochondrial dysfunction in sepsis: Evidence from bacteraemic baboons and endotoxaemic rabbits. *Bioscience Reports* 22:99-113, 2002.
27. Regueira T, Banziger B, Djafarzadeh S, Brandt S, Gorrasi J, Takala J, Lepper P, Jakob S. Norepinephrine to increase blood pressure in endotoxaemic pigs is associated with improved hepatic mitochondrial respiration. *Critical Care* 12: R88, 2008.
28. Binet A, Claret M: Alpha-adrenergic stimulation of respiration in isolated rat hepatocytes. *Biochem J* 283: 867-873, 1983.
29. Stratakos G: Transient lactic acidosis as a side effect of inhaled salbutamol. Chest 122:385-386, 2002.
30. Madiraju A K, Erion D M, Rahimi Y, Zhang X M, Braddock D T, Albright R A, Prigaro B J, Wood J L, Bhanot S, MacDonald M J, Jurczak M J, Camporez J P, Lee H Y, Cline G W, Samuel V T, Kibbey R G, Shulman G I: Metformin suppresses gluconeogenesis by inhibiting mitochondrial glycerophosphate dehydrogenase. *Nature.* 510: 542-6, 2014.

TABLE 1

Oxygen delivery in the 6 groups (ml/min/kg; mean ± SD)

| | Baseline | Septic/sham shock/condition | 3 hrs post | 5 hrs post |
|---|---|---|---|---|
| Non-septic control group (n = 16) | 25 ± 7 | 25 ± 9 | 22 ± 6 | 20 ± 4 |
| Septic control group (n = 13) | 22 ± 7 | 24 ± 8 | 21 ± 9 | 17 ± 9 |
| Gentisic septic group (n = 11) | 18 ± 3 | 26 ± 6 | 20 ± 7 | 20 ± 19 |
| Norepinephrine septic group (n = 10) | 20 ± 3 | 26 ± 11 | 29 ± 8 | 28 ± 10 |
| Gentisic non-septic group (n = 5) | 20 ± 4 | 24 ± 3 | 28 ± 7 | 27 ± 10 |
| Gallic acid septic group (n = 8) | 21 ± 6 | 25 ± 6 | 26 ± 7 | 22 ± 3 |

Statistics by two way ANOVA and Student Newman Keuls' multiple comparison test that included the 6 groups and four time periods. There was a s significant increase (+$P<0.05$) vs septic control group and gentisic septic group

TABLE 2

Galtic acid did not improve hemodynamies in the in vivo septic shock model (mean ± SD) (n = 8)

| | Baseline | Septic shock condition | 3 hrs post treatment | 5 hrs post treatment |
|---|---|---|---|---|
| Mean arterial pressure (mmHg) | 105 ± 14 | 64 ± 12*+ | 71 ± 10*%@!$ | 60 ± 5*%@!$ |
| Cardiac output (L/min/kg) | .113 ± .02 | .15 ± .04 | .12 ± 0.4 | .13 ± .04 |
| Stroke work index ( ml mmHg/Kg) | 212 ± 43 | 72 ± 32*+ | 62 ± 28*+ | 49 ± 20*+ |
| Systemic vascular resistance | 3566 ± 1140 | 1257 ± 89*% | 1673 ± 284*!^% | 1478 ± 222*!^% |

TABLE 2-continued

Galtic acid did not improve hemodynmies in the in vivo septic shock model (mean ± SD) (n = 8)

| | Baseline | Septic shock condition | 3 hrs post treatment | 5 hrs post treatment |
|---|---|---|---|---|
| (dynes S/cm$^5$) | | | | |
| Pulmonary wedge pressure (mmHg) | 11.3 ± 2.3 | 10.4 ± 2.7+ | 11.6 ± 2.6+# | 11.3 ± 2.1+# |
| Heart Rates | 49 ± 3 | 125 ± 28*+ | 125 ± 21*+^ | 127 ± 14*+^ |
| Lactate (nunol/L) | 1.7 ± .5 | 2.3 ± .8 | .8 ± .4#! | .75 ± .35#! |
| Troponin (ng/L) | 0 ± 3 | 14 ± 15 | 41 ± 92 | 69 ± 157* |

Statistics were by ANOVA and SNK including the 6 groups: *P<0.05 vs baseline; +P<0.05 vs non-septic group; #P<0.05 vs Septic control group; % P<0.05 vs Non-septic control group; ^P<0.05 vs Gentisic septic group; !P<0.05 vs Norepinephrine (NE) septic group; $^S$P<0.05 vs GSS non-septic group.

TABLE 3

Selective blood and hematology parameters in the non-septic control group (n = 16)

| | Baseline | Sham shock | 3 hrs posttreatment | 5 hrs posttreatment |
|---|---|---|---|---|
| Hemoglobin (grams/L) | 124 ± 16 | 130 ± 22 | 120 ± 17 | 118 ± 21 |
| WBC (10$^9$/L) | 3.2 ± 1.2@ | 5.2.1 ± 3.9*#@!$^ | 7.43 ± 3.9*#@!$^ | 8.2 ± .3.3*#@!$^ |
| AST (M) | 20 ± 7 | 41 ± 26#! | 53 ± 28#@! | 71 ± 39#@!^ |
| ALT (IU) | 32 ± 15 | 49 ± 31#@! | 61 ± 39#@!^ | 69 ± 48#@!^ |
| LD (IU) | 42 ± 16 | 74 ± 19#@^ | 71 ± 21#@!^ | 86 ± 32#@!^ |
| CK (IU) | 98 ± 27 | 214 ± 220 | 768 ± 830!^ | 1588 ± 1596!$^ |
| Glucose (mmol/L) | 5.5 ± .7 | 6.4 ± 1.0^ | 6.0 ± .6!$ | 6.0 ± 7#@$^ |
| Creatinine clearance (ml/min) | 114 ± .62 | 68 ± 23* | 54 ± 11* | 62 ± 30* |
| Blood urea nitrogen | 5.6 ± 1.4@$^ | 4.6 ± 1.1* | 4.0 ± 1.0*#@ | 3.9 ± 1.0*#@^ |
| Arterial PCO2 (mmHg) | 25 ± 4 | 23 ± 5 | 22 ± 6 | 21 ± 4 |
| Arterial pH | 7.41 ± .05 | 7.37 ± .05#@!^ | 7.36 ± .06#@!^ | 7.35 ± 0.04*#@!^ |
| Mixed venous PO$_2$ | 51 ± 7 | 56 ± 26 | 50 ± 7 | 49 ± 9 |

Mean (±SD). Measurements were obtained at baseline, at the sham shock condition, and after 3 hrs and 5 hrs post placebo treatment. ALT, AST, LD, CK (in international units) are alanine transaminase, aspartate transaminase, lactate dehydrogenase, and creatine kinase respectively. *P<0.05 vs baseline; #P<0.05 vs septic control group; @P<0.05 vs gentisic septic group; !P<0.05 vs norepinephrine septic group; $P<0.05 vs gentisic acid sodium salt non-septic group; ^P<0.05 vs gallic acid septic group by two way analysis of variance and Student Newman Keuls' multiple comparison test.

TABLE 4

Selective blood and hematology parameters in the septic control group (n = 13)

| | Baseline | Septic shock | 3 hrs posttreatment | 5 hrs posttreatment |
|---|---|---|---|---|
| Hemoglobin (grams/L) | 122 ± 14 | 107 ± 36 | 113 ± 39 | 109 ± 35 |
| WBC (10$^9$/L) | 3.6 ± 1.8 | 1.1 ± .6*+$ | 1.3 ± .9*+@!$^ | 0.9 ± .4*+!$ |
| AST (IU) | 38 ± 54 | 159 ± 79*+ | 253 ± 126*+$ | 380 ± 294*+$ |
| ALT (IU) | 59 ± 71 | 155 ± 90+ | 254 ± 149*+$ | 334 ± 202*+@$ |
| LD (IU) | 44 ± 23 | 164 ± 72*+ | 259 ± 84*+$^ | 375 ± 231*+$^ |
| CK (IU) | 219 ± 373 | 406 ± 328 | 1317 ± 2027!^ | 1890 ± 2545!^ |
| Glucose (mmol/L) | 5.3 ± .6 | 5.3 ± 1.4 | 4.7 ± 1.91!$ | 3.1 ± 2.2*+!$^ |
| Creatinine clearance (ml/min) | 99 ± .42 | 52 ± 33 | 22 ± 14* | 15 ± 14* |
| Blood urea nitrogen | 5.3 ± 1@!$^ | 4.8 ± 0.7 | 5.0 ± 0.6+^ | 5.2 ± 0.9+!$^ |
| Arterial PCO2 (mmHg) | 22 ± 3 | 21 ± 6 | 17 ± 4 | 17 ± 5 |
| Arterial pH | 7.39 ± .05 | 7.27 ± .06*+!$^ | 7.21 ± .08*+$ | 7.13 ± 0.12*+@$ |
| Mixed venous PO$_2$ | 50 ± 7 | 53 ± 10 | 53 ± 12 | 52 ± 10 |

Mean (±SD). Measurements were obtained at baseline, at the septic shock condition, and after 3 hrs and 5 hrs post placebo treatment. ALT, AST, LD, CK (in international units) are alanine transaminase, aspartate transaminase, lactate dehydrogenase, and creatine kinase respectively. *P<0.05 vs baseline; +P<0.05 vs non-septic control group; @P<0.05 vs gentisic septic group; !P<0.05 vs norepinephrine septic group; $P<0.05 vs gentisic acid sodium salt non-septic group; ^P<0.05 vs gallic acid septic group by two way analysis of variance and Student Newman Keuls' multiple comparison test.

TABLE 5

Selective blood and hematology parameters in the gentisic septic group (n = 11)

| | Baseline | Septic shock | 3hrs posttreatment | 5 hrs posttreatment |
|---|---|---|---|---|
| Hemoglobin (grams/L) | 112 ± 13 | 108 ± 34 | 125 ± 28 | 130 ± 22 |
| WBC (10$^9$/L) | 2.4 ± 1.4$ | 1.1 ± 0.9+$ | 1.5 ± 1.2+$ | 1.81 ± 1.8+$ |
| AST (IU) | 29 ± 31 | 143 ± 113 | 235 ± 167+$ | 279 ± 208*+!$ |
| ALT (IU) | 51 ± 29 | 161 ± 132 | 209 ± 158+! | 225 ± 171*+# |
| LD (IU) | 36 ± 17 | 150 ± 101* | 267 ± 125*+$^ | 333 ± 139*+$^ |
| CK (IU) | 117 ± 106 | 521 ± 750 | 1847 ± 1763! | 2857 ± 2527*!^ |
| Glucose (mmol/L) | 5.5 ± .4 | 5.3 ± 1.0 | 4.1 ± 1.25!$ | 3.7 ± 2.0+!$ |
| Creatinine clearance (ml/min) | 78 ± 39 | 46 ± 42 | 29 ± 18 | 14 ± 14* |
| Blood urea nitrogen | 6.5 ± 1.9+# | 5.1 ± 1.3*^ | 5.4 ± 1.4*+^ | 5.8 ± 1.6*+$^ |
| Arterial PCO2 (mmHg) | 26 ± 3 | 24 ± 5 | 18 ± 4* | 18 ± 5* |
| Arterial pH | 7.38 ± .03 | 7.26 ± .05*+$ | 7.24 ± .08*+$^ | 7.20 ± 0.06*+#$^ |
| Mixed venous PO$_2$ | 45 ± 6 | 56 ± 7 | 50 ± 6 | 48 ± 7 |

Mean (±SD). Measurements were obtained at baseline, at the septic shock condition, and after 3 hrs and 5 hrs post gentisic acid sodium salt. ALT, AST, LD, CK (in international units) are alanine transaminase, aspartate transaminase, lactate dehydrogenase, and creatine kinase respectively. *P<0.05 vs baseline; +P<0.05 vs non-septic control group; #P<0.05 vs septic control group; !P<0.05 vs norepinephrine septic group; $P<0.05 vs gentisic acid sodium salt non-septic group; ^P<0.05 vs gallic acid septic group by two way analysis of variance and Student Newman Keuls' multiple comparison test.

TABLE 6

Selective blood and hematology parameters in the norepinephrine septic group (n=10)

| | Baseline | Septic shock | 3hrs posttreatment | 5 hrs posttreatment |
|---|---|---|---|---|
| Hemoglobin (grams/L) | 124 ± 15 | 124 ± 43 | 151 ± 13*+#@ | 152 ± 21*+#@ |
| WBC (10$^9$/L) | 3.6 ± 1.7 | 1.4 ± 1.0*+$ | 2.5 ± 1.0+$ | 3.1 ± 2.3+$# |
| AST (IU) | 21 ± 6 | 187 ± 118* | 344 ± 191*+$ | 407 ± 178*+@$ |
| ALT (IU) | 30 ± 8 | 179 ± 157*+ | 305 ± 272*+@$^ | 307 ± 208*+$^ |
| LD (IU) | 43 ± 23 | 177 ± 97*+ | 315 ± 113*+$ | 409 ± 167*+$^ |
| CK (IU) | 106 ± 47 | 1557 ± 3174 | 4573 ± 5173*+#@ | 6273 ± 5789*+#@ |
| Glucose (mmol/L) | 5.9 ± .8 | 4.7 ± 1.5 | 8.1 ± 2.2*+#@ | 7.5 ± 3.9+#@ |
| Creatinine clearance (ml/min) | 127 ± 117 | 41 ± .18* | 30 ± 17* | 24 ± 22* |
| Blood urea nitrogen | 6.1 ± 1.7+^ | 4.9 ± 1.2*^ | 5.5 ± 1.5+^ | 6.2 ± 1.7+#$ |
| Arterial PCO2 (mmHg) | 25 ± 5 | 25 ± 5 | 22 ± 5 | 21 ± 3 |
| Arterial pH | 7.38 ± .05 | 7.26 ± .04*+$ | 7.20 ± .04*+$ | 7.16 ± 0.06*+$ |
| Mixed venous PO$_2$ | 51 ± 6 | 52 ± 4 | 58 ± 8 | 58 ± 7 |

Mean (±SD). Measurements were obtained at baseline, at the septic shock condition, and after 3 hrs and 5 hrs post norepinephrine treatment. ALT, AST, LD, CK (in international units) are alanine transaminase, aspartate transaminase, lactate dehydrogenase, and creatine kinase respectively. *P<0.05 vs baseline; +P<0.05 vs non-septic control group; #P<0.05 vs septic control group; @P<0.05 vs gentisic septic group; $P<0.05 vs gentisic acid sodium salt non-septic group; ^P<0.05 vs gallic acid septic group by two way analysis of variance and Student Newman Keuls' multiple comparison test.

TABLE 7

Selective blood and hematology parameters in the gentisic acid sodium salt (GSS) non-septic group (n = 5)

| | Baseline | Sham shock | 3hrs posttreatment | 5 hrs posttreatment |
|---|---|---|---|---|
| Hemoglobin (grams/L) | 126 ± 8 | 136 ± 11 | 129 ± 6 | 127 ± 11 |
| WBC (10$^9$/L) | 5.4 ± 1.3 | 14 ± 3*+#@!^ | 12 ± 2.3*+#@!^ | 15 ± 2.7*+#@!^ |
| AST (IU) | 24 ± 8 | 41 ± 16^ | 75 ± 27#@^ | 113 ± 25#@!^ |
| ALT (IU) | 74 ± 71 | 90 ± 52 | 92 ± 48#! | 96 ± 50#! |
| LD (IU) | 36 ± 14 | 59 ± 16^ | 91 ± 26@!^ | 135 ± 30#@!^ |
| CK (IU) | 114 ± 32 | 463 ± 173 | 2284 ± 837 | 4297 ± 1218*+ |
| Glucose (mmol/L) | 5.4 ± 2 | 6.2 ± .6 | 8.8 ± 1.6*+#@ | 8.5 ± 2.4+#@ |
| Creatinine clearance (ml/min) | 78 ± 39 | 46 ± 42 | 29 ± 18 | 14 ± 14 |
| Blood urea nitrogen | 6.6 ± 1.7+# | 4.9 ± 0.6*^ | 4.4 ± 0.5*^ | 4.0 ± 0.7*#@!^ |
| Arterial PCO2 (mmHg) | 26 ± 3 | 24 ± 5 | 18 ± 4 | 18 ± 5 |
| Arterial pH | 7.42 ± .07 | 7.38 ± .09*#@!^ | 7.35 ± .04#@!^ | 7.32 ± 0.03#@!^ |
| Mixed venous PO$_2$ | 45 ± 3 | 49 ± 7 | 51 ± 3 | 54 ± 9 |

Mean (±SD). Measurements were obtained at baseline, at the sham shock condition, and after 3 hrs and 5 hrs post GSS. ALT, AST, LD, CK (in international units) are alanine transaminase, aspartate transaminase, lactate dehydrogenase, and creatine kinase respectively. *P<0.05 vs baseline; +P<0.05 vs non-septic control group; #P<0.05 vs septic control group; !P<0.05 vs norepinephrine septic group; @P<0.05 vs gentisic septic group; ^P<0.05 vs gallic acid septic group by two way analysis of variance and Student Newman Keuls' multiple comparison test.

TABLE 8

Selective blood and hematology parameters in the gallic acid septic group (n = 5)

| | Baseline | Septic shock | 3hrs posttreatment | 5 hrs posttreatment |
|---|---|---|---|---|
| Hemoglobin (grams/L) | 128 ± 15 | 138 ± 36 | 145 ± 15 | 137 ± 16 |
| WBC (10$^9$/L) | 3.9 ± 1.2 | 1 ± .6*+$ | 1.2 ± 2.3*+$ | 1.2 ± 1.0*+$ |
| AST (IU) | 19 ± 3 | 241 ± 104*+$ | 324 ± 104*+$ | 363 ± 89*+$ |
| ALT (IU) | 33 ± 16 | 157 ± 61 | 187 ± 68*+! | 189 ± 66*+#! |
| LD (IU) | 36 ± 10 | 200 ± 98*+$ | 415 ± 192*+#@$^ | 513 ± 174*+#@$^ |
| CK (IU) | 104 ± 35 | 2650 ± 3339 | 3832 ± 3896*+# | 5065 ± 3442*+#@ |
| Glucose (mmol/L) | 5.4 ± .4 | 4.0 ± 1.5+ | 8.2 ± 4.5*+#@ | 8.0 ± 4.7*+#@ |
| Creatinine clearance (ml/min) | 108 ± 46 | 42 ± 36* | 28 ± 19* | 17 ± 13* |
| Blood urea nitrogen | 7.26 ± 1.4+#! | 6.5 ± 1.4+#@!$ | 6.7 ± 1.6+#@!$ | 6.9 ± 1.8+#@$ |
| Arterial PCO2 (mmHg) | 25 ± 3 | 25 ± 4 | 22 ± 4 | 23 ± 6 |
| Arterial pH | 7.40 ± .05 | 7.25 ± .10*+$ | 7.17 ± .10*+@$ | 7.12 ± 0.12*+@$ |
| Mixed venous PO$_2$ | 47 ± 4 | 56 ± 9 | 53 ± 6 | 54 ± 12 |

Mean (±SD). Measurements were obtained at baseline, at the septic shock condition, and after 3 hrs and 5 hrs post gallic acid treatment. ALT, AST, LD, CK (in international units) are alanine transaminase, aspartate transaminase, lactate dehydrogenase, and creatine kinase respectively. *P<0.05 vs baseline; +P<0.05 vs non-septic control group; #P<0.05 vs septic control group; ©P<0.05 vs gentisic septic group; !P<0.05 vs norepinephrine septic group; $P<0.05 vs gentisic acid sodium salt non-septic group; by two way analysis of variance and Student Newman Keuls' multiple comparison test.

The invention claimed is:

1. A method of treating an individual who has or is believed to have or at risk of developing lactic acidemia comprising administering to said individual an effective amount of gentisic acid or a pharmaceutically acceptable salt thereof.

2. The method according to claim 1 wherein said individual has sepsis or septic shock.

3. The method according to claim 1 wherein the gentisic acid or pharmaceutically acceptable salt thereof is administered as a pharmaceutical composition in admixture with a suitable pharmaceutically acceptable excipient, diluent or carrier.

4. A method of treating an individual who has or is believed to have or at risk of developing septic shock comprising administering to said individual an effective amount of gentisic acid or a pharmaceutically acceptable salt thereof.

5. The method according to claim 4 wherein the gentisic acid or pharmaceutically acceptable salt thereof is administered as a pharmaceutical composition in admixture with a suitable pharmaceutically acceptable excipient, diluent or carrier.

\* \* \* \* \*